United States Patent [19]

Oi et al.

[11] 4,229,348

[45] Oct. 21, 1980

[54] PENICILLANIC ACID DERIVATIVES

[75] Inventors: Nobuhiro Oi, Hoya; Bunya Aoki, Tama; Teizo Shinozaki, Matsudo; Kanji Moro, Kuki; Isao Matsunaga, Tokyo; Takao Noto, Machida; Toshiyuki Nebashi, Kawagoe; Yusuke Harada, Tokyo; Hisao Endo, Yokohama; Takao Kimura, Chiba; Hiroshi Okazaki, Sayama; Haruki Ogawa, Chofu; Minoru Shindo, Tokyo, all of Japan

[73] Assignee: Chugai Seiyaku Kabushiki Kaisha, Tokyo, Japan

[21] Appl. No.: 5,832

[22] Filed: Jan. 23, 1979

[30] Foreign Application Priority Data

May 26, 1978 [JP] Japan ................................. 53/62164
Jun. 13, 1978 [JP] Japan ................................. 53/70365
Aug. 11, 1978 [JP] Japan ................................. 53/97309
Aug. 29, 1978 [JP] Japan ................................. 53/104362
Sep. 7, 1978 [JP] Japan ................................. 53/109157

[51] Int. Cl.³ .......................................... C07D 499/68
[52] U.S. Cl. .................................. 260/239.1; 424/271
[58] Field of Search ........................................ 260/239.1

[56] References Cited

U.S. PATENT DOCUMENTS

| 3,931,405 | 1/1976 | Eckstrom et al. | 424/271 |
| 3,933,795 | 1/1976 | Disseinkotter et al. | 260/239.1 |
| 3,936,442 | 2/1976 | Konig et al. | 424/239.1 |
| 3,939,149 | 2/1976 | Konig et al. | 260/239.1 |
| 3,959,258 | 5/1976 | Konig et al. | 260/239.1 |
| 3,974,140 | 8/1976 | Konig et al. | 260/239.1 |
| 3,978,223 | 8/1976 | Konig et al. | 424/271 |
| 3,980,792 | 9/1976 | Konig et al. | 424/271 |
| 4,016,282 | 4/1977 | Konig et al. | 424/271 |

FOREIGN PATENT DOCUMENTS

| 1904851 | 5/1970 | Fed. Rep. of Germany | 260/239.1 |
| 2311328 | 10/1973 | Fed. Rep. of Germany | 260/239.1 |
| 1250611 | 1/1969 | United Kingdom | 260/239.1 |
| 1260882 | 1/1972 | United Kingdom | 260/239.1 |
| 1301961 | 1/1973 | United Kingdom | 260/239.1 |
| 1426199 | 2/1976 | United Kingdom | 260/239.1 |

Primary Examiner—Natalie Trousof
Assistant Examiner—Vera C. Clarke
Attorney, Agent, or Firm—Browdy and Neimark

[57] ABSTRACT

Penicillanic acid derivatives which have an excellent antibacterial action particularly against bacteria belonging to family Pseudomonas aeruginosa and are represented by the formula

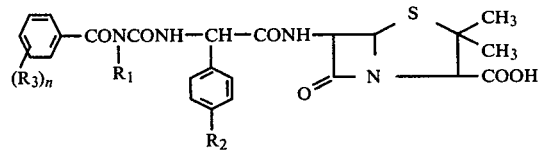

wherein $R_1$, $R_2$, and $R_3$ and n are as defined above, and salts thereof; and a process for preparing the same are disclosed.

19 Claims, No Drawings

PENICILLANIC ACID DERIVATIVES

This invention relates to a penicillanic acid derivative of the formula:

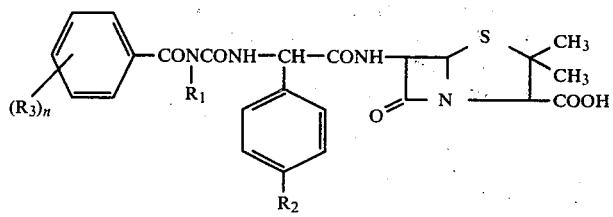

(I)

wherein $R_1$ is a hydrogen atom or a lower alkyl group; $R_2$ is a hydrogen atom or a hydroxyl group; $R_3$ is a hydroxyl group or a lower alkanoyloxy group; n is 2 or 3; at least two of $R_3$ are bonded to adjacent carbon atoms, the position of substituent $R_3$ being selected from 3 to 5 position when $R_1$ is a lower alkyl group and $R_3$ is a hydroxyl group, and 2 to 6 position when $R_1$ and $R_3$ are other substituents, or a salt thereof.

British Pat. No. 1,250,611, U.S. Pat. No. 3,931,405, West German Patent Public Disclosure No. 2,311,328 and Japanese Patent Public Disclosure No. 3532/78 disclose a variety of α-benzoylureido-α-benzylpenicillins, but none of these prior art references make mention of compounds wherein the benzoyl group is substituted by a hydroxyl group or a lower alkanoyloxy group.

British Pat. No. 1,301,961 and No. 1,426,199, as well as U.S. Pat. Nos. 3,933,795, 3,936,442, 3,939,149, 3,959,258, 3,974,140, 3,978,223, 3,980,792 and 4,016,282 disclose a variety of α-benzoylureido-α-benzylpenicillins, but none of them make mention of compounds wherein the benzoyl group is replaced by a hydroxyl group. The definition of substituents for the benzoyl group given in these prior art references include "lower alkanoyloxy" but no further explanation is given that suggests the number of lower alkanoyloxyl groups and bonding to adjacent carbons.

British Pat. No. 1,260,882 discloses α-benzoylureido-α-benzylpenicillins, giving 4-chloro-3-hydroxybenzoyl group, 3-chloro-4-hydroxybenzoyl group, m-hydroxybenzoyl group as examples of the benzoyl group. This prior art reference also discloses p-acetoxybenzoyl group, 2-acetoxy-3-chlorobenzoyl group. o-acetoxybenzoyl group, 2-acetoxy-3-methyl-5-chlorobenzoyl group, 2-acetoxy-5-methylbenzoyl group, 2-acetoxy-4,6-dimethylbenzoyl group, 2-acetoxy-5-t-butylbenzoyl group, 3-methyl-2-pivaloyloxybenzoyl group and 2,4-diacetoxybenzoyl group. However, it makes no mention of a benzoyl group having two or more hydroxyl groups or one having a plurality of adjacent lower alkanoyloxyl groups.

West German Patent Public Disclosure No. 1,904,851 discloses a variety of α-benzoylureido-α-benzylpenicillins. Although it discloses a compound wherein the benzoyl group is replaced by a hydroxyl group, that is, D-α-(N-p-hydroxybenzoylureido)benzylpenicillin, no mention is made of a compound wherein the benzoyl group is substituted by two or more hydroxyl groups or by lower alkanoyloxy groups.

Prior art references that disclose α-benzoylureidoα-benzylpenicillins wherein the benzoyl group has a plurality of adjacent substituents, particularly oxygen-containing groups, are first of all West German Patent Public Disclosure No. 1,904,851 that teaches D-α-(N-3,4-methylenedioxybenzoylureido)benzylpenicillin, and secondly British Pat. No. 1,260,882 that teaches 3,4-dimethoxybenzoyl group, 3,4,5-trimethoxybenzoyl group, and 2,3-dimethoxybenzoyl group as examples of the benzoyl group. However, neither of the two references teaches a compound wherein the benzoyl group has a plurality of adjacent hydroxyl groups or lower alkanoyloxyl groups.

As explained hereinabove, the penicillanic acid derivative of the formula (I) according to this invention is a novel compound which is not disclosed in any of the prior art references.

The penicillanic acid derivative of this invention has in the benzoyl group two to three hydroxyl groups or lower alkanoyloxyl groups at least two of which are adjacent to each other and therefore it is considered to exhibit a better effect than any of the compounds disclosed in the prior art references listed above.

The penicillanic acid derivative of this invention exhibits higher antibacterial activity against bacteria belonging to Pseudomonas in vitro test and animal test than the compounds illustrated in the aforementioned prior art references or carbenicillin considered to be typical of an agent effective against bacteria belonging to Pseudomonas; the derivative also exhibits high ability to prevent infection with such bacteria. In addition, the penicillanic acid derivative of this invention is not only stable under neutral conditions but it is also relatively stable under acidic conditions. Therefore, the penicillanic acid derivative of the formula (I) is an effective antibacterial agent.

The lower alkyl group represented by $R_1$ of the formula (I) has 1 to 4 carbon atoms and may or may not be branched; examples are a methyl group, ethyl group, n-propyl group, isopropyl group, n-butyl group, isobutyl group, t-butyl group, etc. Preferred examples are a methyl group and an ethyl group. The lower alkanoyl group of the lower alkanoyloxyl group represented by $R_3$ has 2 to 4 carbon atoms and may or may not be branched; examples are an acetyl group, propionyl group, n-butyryl group and isobutyryl group. An acetyl group is preferred.

When $R_1$ is a lower alkyl group and $R_3$ is a hydroxyl group, if the hydroxyl group is present on the benzoyl nucleus at 2- or 6-position, the ureido group becomes unstable thus restricting the position of substituent $R_3$. Therefore, when $R_1$ is a lower alkyl group and $R_3$ is a hydroxyl group, the position of substituent $R_3$ is either 3- and 4-position or 3-, 4- and 5-position. For other combinations of $R_1$ and $R_3$, the position of substituent $R_3$ is either 2- and 3-position, 3- and 4-position, 2-, 3- and 4-position, 3-, 4- and 5-position, 2-, 4- and 5-position, 2-, 3- and 5-position or 2-, 3- and 6-position; 2- and 3-position, 3- and 4-position or 3-, 4- and 5-position is preferred.

The penicillanic acid derivative of the formula (I) of this invention has a carboxyl group, and therefore, it is capable of forming salts with various basic substances in said group. All these salts are also covered by the scope of this invention. Examples of a salt of the compound according to this invention are inorganic basic salts, for example, salts of alkali metals such as sodium and potassium, salts of alkaline earth metal such as calcium, and organic basic salts, for example, procain and dibenzylethylenediamine salts. These salts can be prepared by treating a free carboxyl group of the penicillanic acid derivative with the above described inorganic or organic bases.

Due to asymmetric carbon atom in 6-acetoamido group, some end compounds of this invention have their optical isomers, i.e. DL-, D- and L-isomers. All these isomers are also covered by the scope of this invention.

This invention also relates to a process for preparing a penicillanic acid derivative of the formula (I) or its salt.

In accordance with one aspect of this invention, this process comprises reacting a substituted ureidophenylacetic acid of the formula

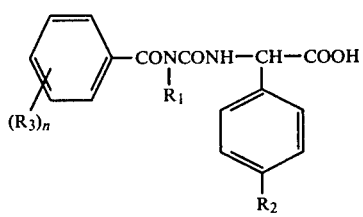

(II)

wherein $R_1$, $R_2$, $R_3$ and n and the positions of $R_3$ are as defined above, or its reactive derivative with 6-aminopenicillanic acid or its reactive derivative to give a penicillanic acid derivative of the formula (I) or its salt.

The reactive derivatives of the substituted ureidophenylacetic acid of the formula (II) means a derivative of said acid the carboxylic group of which is activated for reaction. Examples of said derivatives include acid anhydride, reactive ester or reactive amide. More particularly, they are a mixed acid anhydride with an aliphatic carboxylic acid such as pivalic acid, trichloroacetic acid or pentanoic acid; mixed anhydride with alkyl carbonate; mixed anhydride with phenylphosphoric acid; mixed anhydride with aromatic carboxylic acid; esters such as 1-hydroxybenztriazolyl ester, 2,4-dinitrophenyl ester, N-hydroxysuccinimidyl ester, N-hydroxyphthalimidyl ester, pentachlorophenyl ester, phenylazophenyl ester, cyanomethyl ester and methoxymethyl ester; amides such as those with imidazole, triazole, tetrazole or the like. The reactive derivative of the substituted ureidophenylacetic acid of the formula (II) may be an acid halide if, in the formula (II), $R_3$ is a lower alkanoyloxy group and $R_2$ is a hydrogen atom.

The reactive derivative of penicillanic acid means a derivative of penicillanic acid, 6-amino group of which is activated into reactive form. For example, the introduction of trimethylsilyl into the 6-amino group sufficiently causes the necessary amide-forming reaction.

The amide-forming reaction is generally carried out in a solvent. The solvent which is useful in this reaction is an inert organic solvent such as acetone, tetrahydrofuran, dimethylformamide, pyridine, acetonitrile, dioxane, chloroform, dichloromethane or ethyl acetate. The solvents which are miscible with water may be used as aqueous mixture.

The reaction is generally carried out under cooling, at ambient temperature or under warming, depending on the particular reactants. However, the temperature is usually in the range from $-30°$ to $35°$ C. The reaction time varies from several tens minutes to several tens hours depending on the reaction temperature, particular reactants and solvent used. However, the reaction is generally carried out at a temperature in the range from $-30°$ to $35°$ C. for 0.5 to 48 hours, preferably at $-20°$ to $20°$ C. for 1–24 hours.

Isolation of an object compound from the reaction mixture may be effected by any technique conventionally used for isolation of a penicillin, such as extraction with an organic solvent for example, dichloromethane, chloroform or ethyl acetate; and chromatography on silica gel, an ion-exchange resin, a cross-linked dextran, a high porous polymer of styrene or acrylic ester or the like. The substituted ureidophenylacetic acid of the formula (II) is novel and may be easily prepared, for example, by reacting a corresponding α-aminophenylacetic acid with a benzoyl isocyanate or an N-benzoyl-N-lower alkylcarbamoyl halide of which hydroxyl groups are protected, and if desired, removing the protecting groups. A useful protecting group or technique for removing the group will be illustrated in detail in the explanation for a compound represented by formula (III), particularly, groups of $R_{21}$ and $R_{31}$.

Another aspect of this invention relates to a process for preparing a penicillanic acid derivative of the above formula (I) wherein $R_3$ is a hydroxyl group, and its salt. That is, this process comprises removing protecting groups from a protected penicillanic acid derivative represented by the formula

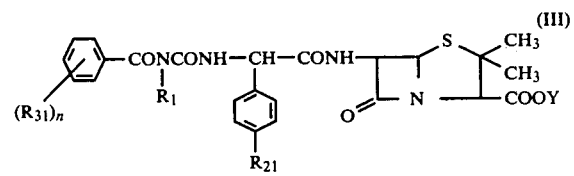

(III)

wherein $R_1$ is a hydrogen atom or a lower alkyl group; $R_{21}$ is a hydrogen atom, a hydroxyl group or a protected hydroxyl group; $R_{31}$ is a hydroxyl group or a protected hydroxyl group; n is 2 or 3; at least two of $R_{31}$ are bonded to adjacent carbon atoms, the position of substituent $R_{31}$ being selected from 3 to 5 position when $R_1$ is a lower alkyl group, and 2 to 6 position when $R_1$ is a hydrogen atom, Y is a hydrogen atom or a protecting group for carboxyl group and at least one of $R_{21}$, $R_{31}$ and Y is a protecting group or is protected, to give a penicillanic acid derivative represented by the formula

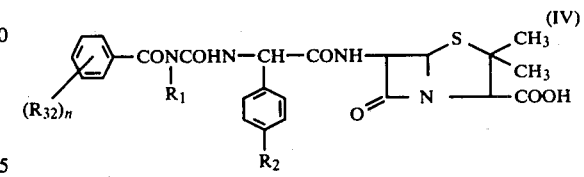

(IV)

wherein n, $R_1$ and $R_2$ are as defined in the formula (I), $R_{32}$ is a hydroxyl group, at least two of $R_{32}$ are bonded to adjacent carbon atoms and the positions of substituent $R_{32}$ is as defined for $R_3$ in the formula (I).

In the formula (III), a hydroxyl protecting group for $R_{21}$ or $R_{31}$ may be any protecting group which can be easily removed under mild conditions. Examples of such protecting group are a lower alkanoyl group such as acetyl, propionyl, butyryl or isobutyryl group.

Although the removal of such lower alkanoyl group may be any conventional way which has been applied for penicillin derivatives, it is desirable to use a technique by which the selectivity for removal of the lower alkanoyl group is excellent and the following purification of the product can be easily carried out. From these viewpoints, a technique using a base is preferable. The base which is useful in this method is an inorganic base such as an ammonium or alkali metal salt of a weak acid, for example, carbonic acid, acetic acid or phosphoric acid, ammonia or an ammonium-form of weakly acidic ion-exchange resin; or an organic base such as a primary-, secondary- or tertiary-lower alkylamine, or a primary-, secondary- or tertiary-amine having one to three lower hydroxy alkyl groups or an alicyclic amine, for example, piperidine or morpholine.

The removal of the protecting groups by this technique is carried out by placing such base in a solvent in the presence of a substance having alcoholic hydroxyl group(s). In this embodiment, it is preferable to use a base which is soluble in the substance having alcoholic hydroxyl group(s) and in the solvent used, preferably a base containing therein at least one basic nitrogen atom, such as ammonia, propylamine, diethylamine, triethylamine, diethylaminoethanol, ethanolamine, triethanolamine, piperidine or morpholine. In addition to these bases, an ammonium form of weakly acidic ion-exchange resin may be used as a suspension in the solvent.

The substance having alcoholic hydroxyl group(s) which may be used includes an alcohol such as methanol, ethanol, ethyleneglycol or glycerine; or a hydroxy lower alkylamine such as diethylaminoethanol, ethanolamine or triethanolamine.

The solvent which can dissolve the salt of the base with the protected penicillanic acid derivative and a penicillanic acid derivative, the object product, may be used. Examples of such solvents are non-protonic polar solvents such as dimethylformamide; and non-polar solvents such as dichloromethane and chloroform. Further, among the substances having alcoholic hydroxy group(s) may be used as a desirable solvent, provided that such substance is adapted to the requirements for the solvent as explained above, for example, methanol and glycerine.

Preferred combinations of the substance with the solvent for proceeding the removal of the protecting group are methanolammonia, triethylamine-triethanolamine-dimethylformamide and the like. The amount of the base varies depending on the number of the protecting groups in the protected penicillanic acid derivative of the formula (III) and the total amount of basic substance present in the reaction system. However, the base is usually present in an amount of 1-15 moles, preferably, 3-10 moles per mole of the protected penicillanic acid derivative.

The amount of the substance having alcoholic hydroxyl group(s) is generally in excess of the amount of the protected penicillanic acid derivative. Although such substance may be used in a large excess amount as a solvent, it is usually used in an amount of 2-10 moles per mole of the protected penicillanic acid derivative when it is not used as solvent. In case a triethylamine-triethanolamine-dimethylformamide system, one of the preferable combinations, is used, triethylamine is used usually in an amount of 0.1-10 moles, preferably, 2-4 moles and triethanolamine, usually 0.7-10 moles, preferably, 3-5 moles, per mole of the protected penicillanic acid derivative. In case a methanol-ammonia system is used, the amount of ammonia is in the range from 1.1-10 moles, preferably, from 2-3 moles per mole of the penicillanic acid derivative and the methanol is in an amount sufficient to act as a solvent.

Although the reaction temperature varies depending on the particular substance having alcoholic hydroxyl group(s), the base and the solvent used, it is usually selected from the range of $-30°$ to $40°$ C. Especially, in case the substance having hydroxyl group(s) also acts as a base, the temperature is usually at $10°$-$40°$ C., preferably at $20°$ to $35°$ C. and in case the substance having hydroxyl group(s) also act as a solvent, the temperature is usually at $-30°$ to $40°$ C., preferably at $-25°$ to $35°$ C.

The reaction time is usually for 30 minutes to 20 hours, preferably 1 to 10 hours.

In addition to the embodiment for removing protecting groups explained above, other techniques for removing the protecting groups from the protected penicillanic acid derivative of the formula (III) may be used. One of such techniques is carried out by using a combination of a nitrogen atom(s) containing-base such as ammonia or primary- or secondary-lower alkylamine with a non-protonic solvent such as dimethylformamide capable of dissolving the salt of the penicillanic acid derivative with such base.

Another technique is to use (a) a base such as an inorganic base such as ammonia, ammonium bicarbonate, ammonium carbonate, ammonium phosphate, ammonium acetate, alkali metal bicarbonate, alkali metal carbonate or alkali metal acetate; an organic base such as ethylamine, diethylamine, triethylamine, piperidine or morpholine; or an ammonium form of weakly acidic ion-exchange resin and (b) a solvent such as water or an aqueous mixture of hydrophilic non-protonic solvent such as dioxane or acetone.

A protecting group for $R_{21}$ in the formula (III) may be a benzyl group. In that case, a benzyl group is removed by catalytic reduction with a palladium-carbon catalyst.

A protecting group for Y in the formula (III) may be a group such as a trimethylsilyl group capable of forming ester with the carboxyl group. The trimethylsilyl group bonded with the carboxyl group is easily removed by the treatment with water or an alcohol. The desirable protecting groups for Y include an organic or inorganic bases capable of forming a salt of the carboxyl group such as alkali metals, alkaline earth metals and tertiary-amines, for example, triethylamine, N-methylpiperidine and pyridine. These bases forming salts are removed by treatment with an acid.

The protected penicillanic acid derivative of the formula (III) can be prepared in various ways. For example, it is prepared by reacting a substituted ureidophenylacetic acid derivative represented by the formula (II) or by the formula

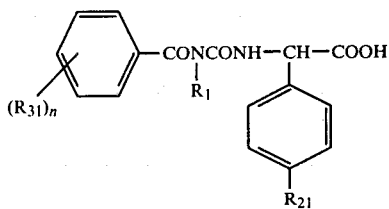 (V)

wherein n, $R_{31}$, $R_1$ and $R_{21}$ are as defined above or its reactive derivative with 6-amino-penicillanic acid or its reactive derivative of the formula

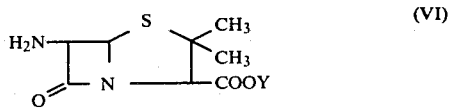 (VI)

wherein Y is as defined in the formula (III). The term "reactive derivative" used for the compounds represented by the formulae (V) and (VI) mean as defined above. The reaction conditions for this amide-formation reaction are those previously explained for the amide-formation reaction.

In case a compound of the formula (VI) wherein Y is a protecting group for carboxyl is used, the amide formation reaction may be carried out effectively by the use of a condensing agent such as a carbodiimide, for example, N,N'-dicyclohexylcarbodiimide, N,N'-diethylcarbodiimide, N-cyclohexyl-N'-morpholinoethylcarbodiimide, N,N'-diisopropylcarbodiimide or the like without previously converting the substituted ureidophenylacetic acid into its reactive derivative.

In this amide-formation reaction, it is matter of course that a substituted ureidophenylacetic acid is reacted with a carbodiimide to activate the carboxyl group prior to the amide-formation reaction.

Alternatively, the protected penicillanic acid derivative of the formula (III) may be prepared by reacting at an α-amino group an α-aminobenzylpenicillanic acid of the formula

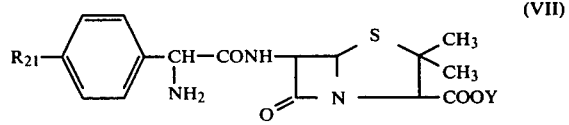 (VII)

wherein $R_{21}$ and Y are as defined for the formula (III) with a benzoyl isocyanate of the formula

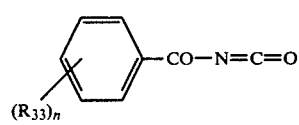 (VIII)

wherein n is 2 or 3 and $R^{33}$ is a protected hydroxyl group, at least two of $R^{33}$ are bonded to adjacent carbon atoms, the position of substituent being selected from 2–6 position, or with an N-benzoylcarbamoyl halide of the formula

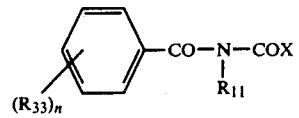 (IX)

wherein n and $R_{33}$ are as defined above except that the position of $R_{33}$ is selected from 3–5 position and X is a halogen atom and $R_{11}$ is a lower alkyl.

Further, the protected penicillanic acid derivative of the formula (III) wherein $R_{21}$ is a hydrogen atom may be prepared by reacting an α-ureido-benzylpenicillin or its reactive derivative of the formula

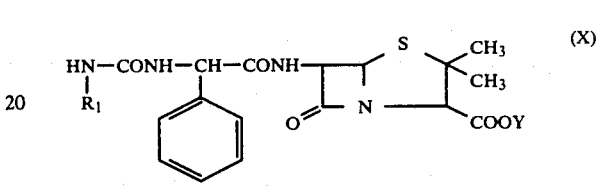 (X)

wherein $R_1$ and Y are as defined above, with a benzoyl halide of the formula

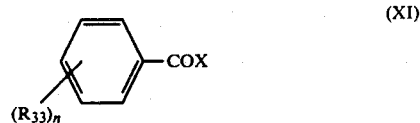 (XI)

wherein n, $R_{33}$ and X are as defined above.

Another aspect of this invention relates to a process for preparing a penicillanic acid derivative of the formula (I) wherein $R_3$ is a lower alkanoyloxyl group, or its salt. That is, the feature of the process of this aspect is in preparing a penicillanic acid derivative of the formula

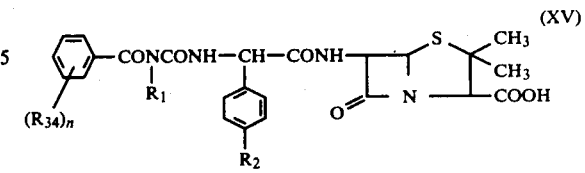 (XV)

wherein n, $R_1$ and $R_2$ are as defined for the formula (I) and $R_{34}$ is as defined for the formula (XIII), or its salt by reacting an α-aminobenzylpenicillin or its reactive derivative of the formula

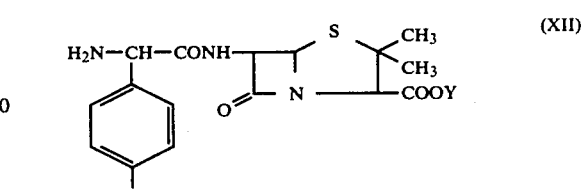 (XII)

wherein $R_2$ is as defined for the formula (I) and Y is a hydrogen atom or a protecting group for carboxyl group, with a benzoyl isocyanate of the formula

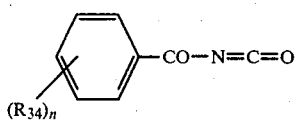

(XIII)

wherein n is 2 or 3 and $R_{34}$ is a lower alkanoyloxy group, at least two of them being bonded to adjacent carbon atoms, or with a benzoylcarbamoyl halide of the formula

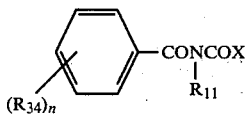

(XIV)

wherein n and $R_{34}$ are as defined above; $R_{11}$ is a lower alkyl group and X is a halogen atom, and if necessary, converting Y to a hydrogen atom.

In the explanation of this process, a reactive derivative of an α-aminobenzylpenicillin means a derivative in which an α-amino group is activated, for example, by introduction of a trimethylsilyl group at the amino group.

The particular protecting group for Y in the formula (XII) and a technique for removing the protecting group are the same as those disclosed in the explanation with respect to the formula (III). In the case of the reaction with a benzoyl isocyanate of the formula (XIII), a penicillanic acid derivative of the formula (XV) wherein $R_1$ is a hydrogen atom is produced. If a benzoylcarbamoyl halide of the formula (XIV) is reacted, the derivative of the formula (XV) wherein $R_1$ is a lower alkyl group is produced.

The reaction is generally carried out in a solvent. The solvent which is useful in this reaction is an inert organic solvent such as dichloromethane, 1,2-dichloroethane, chloroform, acetonitrile, acetone, tetrahydrofuran, ethyl acetate, dioxane or the like. Any solvent which is miscible with water may be used as an aqueous mixture.

The reaction is generally carried out under cooling, at ambient temperature or under heating, depending on the particular reactants and the solvent used. However, the reaction temperature is usually in the range of −30° to 35° C. preferably, −10° to 20° C. The reaction time varies from several tens minutes to several tens hours, depending on the temperature and solvent used. However, the reaction is usually carried out in the range of −30° to 35° L C. for several tens minutes to 24 hours, preferably at −10° to 20° C. for 0.5–5 hours.

Isolation of an object compound from the reaction mixture may be effected by any technique conventionally used for isolation of a penicillin, such as extraction with an organic solvent for example, dichloromethane, chloroform or ethyl acetate; and chromatography on silica gel, an ion-exchange resin, a cross-linked dextran, a high porous polymer of stylene or acrylic ester or the like.

In accordance with still another aspect of this invention, a process for preparing a penicillanic acid derivative of the formula (I) wherein $R_2$ is a hydrogen atom and $R_3$ is a lower alkanoyl-oxyl group or its salt is provided. This process comprises reacting an α-ureidobenzylpenicillin of the formula

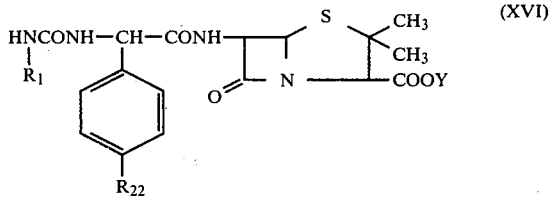

(XVI)

wherein $R_1$ is as defined above for the formula (I), $R_{22}$ is a hydrogen atom and Y is a hydrogen atom or a protecting group for carboxyl group, or its reactive derivative with a benzoyl halide of the formula

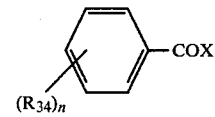

wherein n and $R_{34}$ are as defined above for the formula (XIII) and X is a halogen atom and, if necessary, converting Y to a hydrogen atom to give a penicillanic acid derivative of the formula (XV) wherein $R_2$ is a hydrogen atom or its salt.

The reactive derivative of the α-ureidobenzylpenicillin of the formula (XVI) is a derivative of the penicillin, the terminal amino group of which is activated into a reactive form. For example, the activation is made by the introduction of a trimethylsilyl group.

The particular protecting group for Y in the formula (XVI) and a technique for removing the protecting group which are useful in this process are the same as those explained as for the formula (III).

The reaction is generally carried out in a solvent. The solvent which is useful in this reaction is an inert organic solvent such as dichloromethane, 1,2-dichloroethane, chloroform, acetonitrile, acetone, tetrahydrofuran, ethyl acetate, dioxane or the like. Any solvent which is miscible with water may be used as an aqueous mixture.

The reaction is generally carried out under cooling or at ambient temperature, depending on the particular reactants and the solvent used. However, the reaction temperature is usually in the range of −10° to ambient temperature, preferably 0° to 10° C. The reaction time varies from several tens minutes to several tens hours, depending on the temperature and solvent used. However, the reaction is usually carried out in the range of −10° C. to ambient temperature for 1–48 hours, preferably at 0° to 10° C. for 1–10 hours.

Isolation of an object compound from the reaction mixture may be effected by any technique conventionally used for isolation of a penicillin, such as extraction with an organic solvent for example, dichloromethane, chloroform or ethyl acetate; and chromatography on silica gel, an ion-exchange resin, a cross-linked dextran, a high porous polymer of stylene or acrylic ester or the like.

An optical isomer such as D- or L-isomer of the object compound of the formula (I) can be prepared by using an optically active starting compound as an amino acid or a substituted ureidophenyl acetic acid which is prepared by a usual optical resolution technique, for example, a technique reported in J. P. Greenstein, M.

Winitz, "Chemistry of the Amino Acids", Vol. 1, pp. 715–760, John Wiley and Sons, N.Y. (1961).

The object compound of this invention can be formulated into various pharmaceutical preparations adapted to various administration routes in a manner similar to that used for other penicillin compounds. Therefore, one aspect of this invention involves a pharmaceutical composition for human beings or animals. The preparation is provided by using a conventional pharmaceutical carrier, diluent and/or excipient.

In particular, an emulsion, solution or suspension in an aqueous or oily vehicle can be formulated for injection. Suppository is also given by using a conventional suppository base such as coconut oil or other glycerides.

The content of the active compound varies depending on the administration route, but is usually above 0.1% such as 5–99%, preferably 10–60%.

The amount of administration for human being is usually in the range of 100 to 3000 mg per day for an adult. The administration in an amount ranging from 500 to 2000 mg per day is preferable for an adult though the amount varies depending on body weight, age, symptom, route of administration or frequency of administration.

Minimum inhibitory concentration (MIC) for several kinds of bacteria was determined with respect to several compounds of this invention and carbenicillin (carboxybenzylpenicillin) and the results are shown in the following table. The compounds tested are as follows:

(1) 6-[D(−)-α-{3-(2,3-dihydroxybenzoyl)-1-ureido}-α-phenylacetamide]penicillanic acid.

(2) 6-[D(−)-α-{3-(3,4-dihydroxybenzoyl)-1-ureido}-α-phenylacetamide]penicillanic acid.

(3) 6-[D(−)-α-{3-(3,4-dihydroxybenzoyl)-1-ureido}-α-(4-hydroxyphenyl)acetamide]penicillanic acid.

(4) 6-[D(−)-α-{3-(3,4,5-trihydroxybenzoyl)-1-ureido}-α-phenylacetamide]penicillanic acid.

(5) 6-[D(−)-α-{3-(3,4-dihydroxybenzoyl)-3-methyl-1-ureido}-α-(4-hydroxyphenyl)acetamido]penicillanic acid.

(6) 6-[D(−)-α-{3-(3,4-dihydroxybenzoyl)-3-methyl-1-ureido}-α-phenylacetamido]penicillanic acid.

(7) 6-[D(−)-α-{3-(3,4,5-trihydroxybenzoyl)-3-methyl-1-ureido}-α-phenylacetamido]penicillanic acid.

(8) 6-[D(−)-α-{3-(3,4-dihydroxybenzoyl)-3-ethyl-1-ureido}-α-phenylacetamido]penicillanic acid.

(9) 6-[D(−)-α-{3-(3,4-diacetoxybenzoyl)-3-methyl-1-ureido}-α-phenylacetamido]penicillanic acid.

(10) 6-[D(−)-α-{3-(3,4-diacetoxybenzoyl)-3-methyl-1-ureido}-α-(4-hydroxyphenyl)acetamido]penicillanic acid.

(11) 6-[D(−)-α-{3-(3,4-diacetoxybenzoyl)-1-ureido}-α-phenylacetamido]penicillanic acid.

(12) 6-[D(−)-α-{3(3,4-diacetoxybenzoyl)-1-ureido}-α-(4-hydroxyphenyl)acetamido]penicillanic acid.

(13) 6-[D(−)-α-{3-(3,4,5-triacetoxybenzoyl)-1-ureido}-α-phenylacetamido]penicillanic acid.

| | (1) | (2) | (3) | (4) | (5) | (6) | (7) | (8) | (9) | (10) | (11) | (12) | (13) | Carbenicillin |
|---|---|---|---|---|---|---|---|---|---|---|---|---|---|---|
| Bacillus subtilis PCI-219 | 0.4 | 0.1 | ≦0.05 | 0.4 | ≦0.78 | ≦0.78 | ≦0.78 | ≦0.78 | <0.09 | 0.2 | ≦0.1 | ≦0.1 | 0.4 | ≦0.78 |
| Staphylococcus aureus 209 P | 0.4 | 0.1 | 0.2 | 0.4 | ≦0.78 | ≦0.78 | 1.56 | ≦0.78 | 0.19 | 0.4 | ≦0.1 | 0.2 | 0.2 | ≦0.78 |
| Staphylococcus aureus JU-5 | 6.25 | 3.12 | 3.12 | 100 | 6.25 | 3.12 | 25 | 12.5 | 6.25 | 6.25 | 3.12 | 3.12 | 12.5 | 6.25 |
| Sarcina lutea B | 0.1 | <0.05 | <0.05 | 0.1 | ≦0.78 | ≦0.78 | ≦0.78 | ≦0.78 | <0.09 | ≦0.1 | ≦0.1 | ≦0.1 | ≦0.1 | ≦0.78 |
| Escherichia coli NIHJ | 0.1 | 0.4 | 0.1 | 1.56 | ≦0.78 | ≦0.78 | 0.78 | ≦0.78 | <0.09 | 0.2 | 0.4 | 0.4 | 3.12 | 3.12 |
| Shigella flexneri 2b | 0.2 | 0.4 | 0.1 | 50 | ≦0.78 | ≦0.78 | 1.56 | ≦0.78 | <0.09 | ≦0.1 | 0.78 | 0.2 | 3.12 | 1.56 |
| Salmonella paratyphi A | 0.4 | 0.2 | <0.05 | 0.70 | ≦0.78 | ≦0.78 | 1.56 | ≦0.78 | ≦0.19 | ≦0.1 | 0.2 | 0.1 | 0.4 | ≦0.78 |
| Klebsiella pneumoniae 15C | 1.56 | 6.25 | 1.56 | 200 | <3.12 | ≦0.78 | 6.25 | 1.56 | 0.39 | 3.12 | 6.25 | 3.12 | 200 | 200 |
| Proteus mirabilis 9' | 0.78 | 1.56 | 0.78 | 50 | 0.78 | 0.78 | 3.12 | 1.56 | 0.78 | 0.78 | 1.56 | 1.56 | 3.12 | ≦0.78 |
| Pseudomonas aeruginosa J-272 | <0.05 | 0.2 | 0.1 | 0.78 | ≦0.78 | ≦0.78 | 12.5 | 0.78 | 0.39 | 0.2 | 0.4 | 0.4 | 0.4 | 200 |
| pseudomonas aeruginosa J-169 | 0.2 | 0.4 | 0.2 | 1.56 | ≦0.78 | ≦0.78 | 6.25 | 3.12 | 0.78 | 0.2 | 0.4 | 0.4 | 0.4 | 400 |
| Pseudomonas aeruginosa J-169-CM222 | 0.78 | 1.56 | 3.12 | 12.5 | 0.78 | 1.56 | 12.5 | 6.25 | 3.12 | 0.4 | 1.56 | 0.78 | 1.56 | 400 |
| Pseudomonas aeruginosa KAN-2 | 0.1 | 0.1 | <0.05 | 0.4 | ≦0.78 | ≦0.78 | 1.56 | 0.78 | 0.19 | 0.1 | 0.2 | 0.1 | 0.2 | 50 |
| Pseudomonas aeruginosa GNB-78 | <0.05 | 0.2 | <0.05 | 0.4 | ≦0.78 | ≦0.78 | 3.12 | 0.78 | 0.39 | 0.1 | 0.2 | 0.1 | 0.2 | 25 |
| Pseudomonas aeruginosa GNB-75 | <0.05 | 0.1 | <0.05 | 0.2 | ≦0.78 | ≦0.78 | 1.56 | ≦0.78 | <0.09 | 0.2 | 0.2 | 0.1 | 0.2 | 0.78 |
| Pseudomonas aeruginosa GNB-75-M57740 | <0.05 | <0.05 | <0.05 | <0.05 | ≦0.78 | ≦0.78 | ≦0.78 | ≦0.78 | <0.09 | ≦0.1 | ≦0.1 | ≦0.1 | ≦0.1 | 0.39 |

The processes for preparing some of the compounds of this invention are illustrated by the following Examples.

EXAMPLE 1

(1) Oxalyl chloride (10.1 g) was added to a solution of 3,4-diacetoxybenzamide (7.5 g) in 1,2-dichloroethane (80 ml) with stirring under cooling. The mixture was gradually heated to a reflux temperature and allowed to react under reflux for 13 hours. After completion of the reaction, the solvent and excess oxalyl chloride was distilled off under reduced pressure to give 3,4-diacetoxybenzoyl isocyanate which was dissolved in anhydrous dichloromethane (40 ml) for the subsequent reaction.

(2) N,O-bis(trimethylsilyl)acetamide (40 ml) was added dropwise to a suspension of ampicillin trihydrate (12.8 g) in anhydrous dichloromethane (100 ml) at room temperature, followed by stirring until the mixture was made clear. The solution in dichloromethane previously formed in (1) above was added dropwise to the clear solution obtained while maintaining its temperature between 5°–10° C. followed by stirring the mixture at the same temperature for 2 hours. Then, the mixture was evaporated to dryness under reduced pressure at room temperature and to the residue was added anhydrous methanol and the mixture was evaporated again to dryness under reduced pressure. Ethyl acetate (300 ml) and cold 2 N hydrochloric acid (100 ml) were added to the residue and the organic layer was separated. The organic layer separated was washed with water and extracted three times with a cold saturated aqueous solution of sodium bicarbonate in a total amount of 200 ml. The combined aqueous layer was washed with ethyl acetate (200 ml) and, after adjusting its pH to about 2.5 with cold 2 N hydrochloric acid, re-extracted with ethyl acetate (150 ml). The organic layer separated was washed with a cold saturated sodium chloride aqueous solution, dried over anhydrous sodium sulfate, treated with active charcoal and concentrated by evaporation at room temperature under reduced pressure. The residue was treated with n-hexane (80 ml) to give 8.0 g of 6-[D(—)-α-{3-(3,4-diacetoxybenzoyl)-1-ureido}-α-phenylacetamido]penicillanic acid as a pale yellow amorphous solids.

| TLC: | Rf 0.43, silica gel 60 $F_{254}$ |
|---|---|
| Carrier: | (a pre-coated plate manufactured by E. Merk, Darmstadt) |
| Developer: | ethyl acetate-ethanol-acetic acid (25:5:1 by volume) |
| IR spectrum: | $\nu_{max}^{KBr}(cm^{-1})$ 3,700–2,300, 1,770, 1,700–1,620, 1,525, 1,490 |
| NMR spectrum: | (DMSO-$d_6$, 60MHz) δ(ppm) 1.42(3H,s), 1.54(3H,s), 2.28(6H,s), 4.23(1H,s), 5.3–6.1(3H,m), 7.0–8.0(8H,m). |

EXAMPLE 2

In 30 ml of methanol was dissolved 6-[D(—)-α-{3-(3,4-diacetoxybenzoyl)-1-ureido{-α-phenylacetamido]-penicillanic acid (2.0 g) obtained in Example 1 and 3.7 ml of methanolic ammonia (0.075 g/ml) was added dropwise to the solution with stirring and keeping its temperature within the range from −15° to −10° C. The stirring was continued for 75 minutes while allowing the temperature of the mixture to gradually rise to about 0° C. to complete the reaction. Then, the reaction mixture was added to a mixture of 150 ml of a 5% aqueous hydrochloric acid and 150 ml of ethyl acetate while stirring under cooling with ice water. The organic layer was separated from the mixture and extracted with 100 ml of a cold, saturated aqueous solution of sodium bicarbonate. The aqueous layer separated was washed with ethyl acetate and, after adjusting its pH to about 2.5 with cold 2 N hydrochloric acid, reextracted with 100 ml of ethyl acetate. The organic layer separated was washed with a cold, saturated sodium chloride aqueous solution, dried over anhydrous magnesium sulfate and concentrated by evaporation at room temperature under reduced pressure. The residue was treated with 80 ml of n-hexane to give 1.2 g of 6-[D(—)-α-3{(3,4-dihydroxybenzoyl)-1-ureido}-α-phenylacetamido]-penicillanic acid as a pale yellow amorphous solid.

| TLC: | Rf 0.39, silica gel 60$F_{254}$ |
|---|---|
| Carrier: | (a pre-coated plate manufactured by E. Merck, Darmstadt) |
| Developer: | ethyl acetate-ethanol-acetic acid (25:5:1, by volume) |
| IR spectrum: | $\nu_{max}^{KBr}(cm^{-1})$ 3,700–2,300, 1,770, 1,740, 1,690–1,620, 1,550–1,480 |
| NMR spectrum: | (DMSO-$d_6$, 60MHz) δ(ppm) 1.41(3H,s), 1.53(3H,s), 4.22(1H,s), 5.3–6.0 (3H,m), 6.6–7.7(8H,m). |
| UV spectrum: | ($C_2H_5OH$) λmax (nm) 260, 295 |
| Color reaction with ferric chloride: | positive (dark green) |

EXAMPLE 3

The procedure used in Example 1 (2) was repeated except that amoxicillin trihydrate (13.1 g) was used instead of ampicillin trihydrate (12.8 g) to give 9.0 of 6-[D(—)-α-{3-(3,4-diacetoxybenzoyl)-1-ureido}-α-(4-hydroxyphenyl)acetamido]penicillanic acid as a pale yellow amorphous solid.

| TLC: | Rf 0.40, silica gel 60 $F_{254}$ |
|---|---|
| Carrier: | (a pre-coated plate manufactured by E. Merck, Darmstadt) |
| Developer: | ethyl acetate-ethanol-acetic acid (25:5:1, by volume) |
| IR spectrum: | $\nu_{max}^{KBr}(cm^{-1})$ 3,700–2,300, 1,770, 1,710–1,630, 1,550–1,450 |
| NMR spectrum: | (DMSO-$d_6$, 60MHz) δ(ppm) 1.47(3H,s), 1.56(3H,s), 2.28(6H,s), 4.24(1H,s), 5.3–6.0(3H,m), 6.6–8.2(7H,m). |

EXAMPLE 4

The procedure used in Example 2 was repeated except that 6-[D(—)-α-{3-(3,4-dicaetoxybenzoyl)-1-ureido}-α-(4-hydroxyphenyl)acetamido]penicillanic acid (2.0 g) obtained in Example 3 was used instead of 6-[D(—)-α-{3-(3,4-diacetoxybenzoyl)-1-ureido}-α-phenylacetamido]penicillanic acid (2.0 g) to give 1.1 g of 6-[D(—)-α-{3-(3,4-dihydroxybenzoyl)-1-ureido}-α-(4-hydroxyphenyl)acetamido]penicillanic acid as a pale yellow amorphous solid.

| TLC: | Rf 0.35, silica gel 60$F_{254}$ |
|---|---|
| Carrier: | (a pre-coated plate manufactured by E. Merck, Darmstadt) |
| Developer: | ethyl acetate-ethanol-acetic acid (25:5:1, by volume) |
| IR spectrum: | $\nu_{max}^{KBr}(cm^{-1})$ 3,700–2,300, 1,770, 1,740–1,630, 1,560–1,480 |
| NMR spectrum: | (DMSO-$d_6$, 60MHz) δ(ppm) 1.43(3H,s), 1.57(3H,s), 4.22(1H,s), 5.3–5.9 (3H,m), 6.5–7.6(7H,m). |
| UV spectrum: | ($C_2H_5OH$) λmax (nm) 266, 295 |

| | |
|---|---|
| Color reaction | positive (dark |
| with ferric | green) |
| chloride: | |

EXAMPLE 5

(1) The procedure used in Example 1 (1) was repeated except that 3,4,5-triacetoxybenzamide (8.0 g) and oxalyl chloride (8.6 g) were used instead of 3,4-diacetoxybenzamide (7.5 g) and oxalyl chloride (10.1 g) to give a solution of 3,4,5-triacetoxybenzoyl isocyanate in anhydrous dichloromethane (40 ml).

(2) Ampicillin trihydrate (10.9 g) was reacted with the isocyanate obtained in (1) above in a manner as in Example 1 (2) to give 5.0 g of 6-[D(−)-α-{3-(3,4,5-triacetoxybenzoyl)-1-ureido}-α-phenylacetamido]-penicillanic acid as a pale brown amorphous solid.

| | |
|---|---|
| TLC: | Rf 0.41, silica gel 60F$_{254}$ |
| Carrier: | (a pre-coated plate manufactured by E. Merck, Darmstadt) |
| Developer: | ethyl acetate-ethanol-acetic acid (25:5:1, by volume) |
| IR spectrum: | $v_{max}^{KBr}$(cm$^{-1}$) 3,700–2,300, 1,775, 1,700–1,600, 1,520, 1,485 |
| NMR spectrum: | (DMSO-d$_6$, 60MHz) δ(ppm) 1.46(3H,s), 1.55(3H,s), 2.30(9H,s), 4.26(1H,s), 5.3–6.1(3H,m), 7.2–7.7(5H,m), 7.83(2H,s). |

EXAMPLE 6

6-[D(−)-α-{3-(3,4,5-Triacetoxybenzoyl)-1-ureido}-α-phenylacetamido]penicillanic acid (2.2 g) obtained in Example 5 was dissolved in methanol (30 ml) and to the solution was added dropwise 3.7 ml of methanolic ammonia (0.075 g/ml) with stirring and maintaining its temperature between −15° and −12° C. The stirring was continued for 40 minutes while allowing the temperature of the mixture to gradually rise to a temperature between −9° and −8° C. to complete the reaction. Then, the reaction mixture was added to a mixture of 5% hydrochloric acid (150 ml) and ethyl acetate (150 ml) while stirring under cooling with ice-water. The organic layer separated was extracted with a cold, saturated sodium bicarbonate aqueous solution (100 ml). The aqueous layer separated was washed with ethyl acetate and, after adjusting its pH to about 2.5 with cold 2 N hydrochloric acid, reextracted with 100 ml of ethyl acetate. The ethyl acetate layer was washed with a cold, saturated sodium chloride aqueous solution and dried over anhydrous magnesium sulfate. After the solvent was distilled off at room temperature under reduced pressure, 20 ml of ethyl acetate was added to the residue and the insoluble solids were filtered off. The filtrate was triturated with n-hexane (100 ml) to give 1.0 g of 6-[D(−)-α-{3-(3,4,5-trihydroxybenzoyl)-1-ureido}-α-phenylacetamido]penicillanic acid as light yellow amorphous solid.

| | |
|---|---|
| TLC: | Rf 0.34, silica gel 60F$_{254}$ |
| Carrier: | (a pre-coated plate manufactured by E. Merck, Darmstadt) |
| Developer: | ethyl acetate-ethanol-acetic acid (25:5:1, by volume) |
| IR spectrum: | $v_{max}^{KBr}$(cm$^{-1}$) 3,700–2,300, 1,770, 1,750–1,630, 1,560–1,470 |
| NMR spectrum: | (DMSO-d$_6$, 60MHz) δ(ppm) 1.42(3H,s), 1.53(3H,s), 4.23(1H,s), 5.3–6.0 (3H,m), 6.8–7.7(7H,m). |
| UV spectrum: | (C$_2$H$_5$OH) λmax (nm) 268 |
| Color reaction with ferric chloride: | positive (dark blue) |

EXAMPLE 7

(1) Oxalyl chloride (5.3 g) was added to a solution of 2,3-diacetoxybenzamide (4.0 g) in 1,2-dichloroethane (40 ml) with stirring under cooling. The mixture was gradually heated to a reflux temperature and allowed to react under reflux for 10 hours. Then, the solvent and excess oxalyl chloride were distilled off under reduced pressure to give 2,3-diacetoxybenzoyl isocyanate, which was dissolved in anhydrous dichloromethane (40 ml) for the subsequent reaction.

(2) N,O-Bis(trimethylsilyl)acetamide (19 ml) was added dropwise at room temperature to a suspension of D(−)-phenylglycine (5.3 g) in anhydrous dichloromethane (100 ml) at room temperature followed by stirring until the mixture was made clear. The solution previously obtained in (1) above was added dropwise to the clear solution at a temperature of from 5° to 10° C. After stirring the mixture for 1.5 hours at the same temperature, the mixture was evaporated to dryness at room temperature under reduced pressure. To the residue was added anhydrous methanol and evaporated to dryness under reduced pressure. To the residue was added cold diluted aqueous hydrochloric acid (200 ml) and the mixture was stirred for 5 to 10 minutes. The resulting white precipitates were collected by filtration and dissolved in a cold, saturated sodium bicarbonate aqueous solution (250 ml), and the insoluble substances were removed by filtration. The filtrate was washed with ethyl acetate (250 ml) and, after adjusting its pH to about 2.5 with cold 2 N hydrochloric acid, the resulting white precipitates were collected by filtration, washed with water and then diethyl ether, and air-dried at room temperature to give 4.5 g of D(−)-α-[3-2,3-diacetoxybenzoyl)-1-ureido]-α-phenylacetic acid as a white powder. m.p. 200°–201° C. (decomposition). Analysis:

Calcd. for C$_{20}$H$_{18}$N$_2$O$_8$: C, 57.97; H, 4.38; N, 6.76 (%). Found: C, 57.64; H, 4.39; N, 6.65 (%).

(3) D(−)-α-[3-(2,3-Diacetoxybenzoyl)-1-ureido]-α-phenylacetic acid (2.0 g) was suspended in methanol (20 ml) and to the solution was added dropwise 29% aqueous ammonia (2.5 ml) under cooling with ice-water. The mixture was stirred at 5° to 10° C. for 30 minutes and concentrated at room temperature under reduced pressure. To the residue were added ethyl acetate (50 ml) and a cold, saturated sodium bicarbonate aqueous solution (100 ml). The aqueous layer was separated and, after removal of the insoluble substances by filtration, its pH was adjusted to about 2.5 with cold 2 N hydrochloric acid. The resulting white precipitate was collected by filtration, washed with water and then diethyl ether, and air-dried to give 1.4 g of D(−)-α-[3-(2,3-dihydroxybenzoyl)-1-ureido]-α-phenylacetic acid as white powder. m.p. 211°–212° C. (decomposition). Analysis:

Calcd. for C$_{16}$H$_{14}$N$_2$O$_6$·H$_2$O: C, 55.17; H, 4.63; N, 8.04 (%). Found: C, 55.44; H, 4.38; N, 8.08 (%).

(4) D(−)-α-[3-(2,3-Dihydroxybenzoyl)-1-ureido]-α-phenylacetic acid (1.0 g) and 1-hydroxybenztriazole (0.41 g) were dissolved in anhydrous tetrahydrofuran (100 ml) and to the solution was added dropwise at 0° to 5° C. a solution of N,N'-dicyclohexylcarbodiimide (0.75 g) in anhydrous tetrahydrofuran (10 ml). The mixture was stirred while allowing its temperature to gradually rise to room temperature and, about 2.5 hours after, the precipitating dicyclohexylurea was removed by filtration. The filtrate containing 1-benztriazolyl ester of D(−)-α-[3-(2,3-dihydroxybenzoyl)-1-ureido]-α-phenylacetic acid was used for the subsequent reaction.

(5) N,O-Bis(trimethylsilyl)acetamide (3.0 ml) was added at 15° to 20° C. under a nitrogen atmosphere to a suspension of 6-aminopenicillanic acid (1.30 g) in anhydrous dichloromethane (50 ml) followed by stirring until the mixture was made clear. To the clear solution was added dropwise the tetrahydrofuran solution previously obtained in (4) above while maintaining its temperature at 5° to 10° C. followed by stirring the mixture at the same temperature for 2 hours. Then, the mixture was evaporated to dryness at room temperature under reduced pressure and, to the residue was added anhydrous methanol, evaporated again to dryness under reduced pressure. Ethyl acetate (150 ml) and cold N hydrochloric acid (100 ml) were added to the residue and then the organic layer was recovered. The organic layer was washed with a cold, saturated sodium chloride aqueous solution and extracted three times with a cold, saturated sodium bicarbonate aqueous solution in a total amount of 150 ml. The resulting aqueous layer was washed with ethyl acetate (150 ml) and, after adjusting its pH to about 2.5 with cold 2 N hydrochloric acid, re-extracted with ethyl acetate (150 ml). The organic layer was washed with a cold, saturated sodium chloride aqueous solution, dried over anhydrous sodium sulfate and concentrated under reduced pressure. The residue was treated with 80 ml of n-hexane to give 1.0 g of 6-[D(−)-α-{3-(2,3-dihydroxybenzoyl)-1-ureido}-α-phenylacetamido]-penicillanic acid as a amorphous white solids.

| TLC: | Rf 0.37, silica gel 60 $F_{254}$ |
|---|---|
| | Carrier: (a pre-coated plate manufactured by E. Merck, Darmstadt) |
| | Developer: ethyl acetate-ethanol-acetic acid (25:5:1, by volume) |
| IR spectrum: | $\nu_{max}^{KBr}(cm^{-1})$ 3,700–2,300, 1,770, 1,745–1,625, 1,560–1,450 |
| NMR spectrum: | (DMSO-$d_6$, 60MHz) δ(ppm) 1.41(3H,s), 1.56(3H,s), 4.23(1H,s), 5.3–6.0 (3H,m), 6.6–7.7(8H,m). |
| UV spectrum: | ($C_2H_5OH$) λmax (nm) 254, 322 |
| Color reaction with ferric chloride: | positive (dark green) |

EXAMPLE 8

(1) A solution of triethylamine (6.04 g) in anhydrous dichloromethane (20 ml) was added dropwise at room temperature to a solution of N-methyl-3,4-diacetoxybenzamide (15.0 g) and trimethylsilyl chloride (6.49 g) in anhydrous dichloromethane (70 ml). After the mixture was refluxed for 20 minutes, a solution of phosgene (42 ml) in anhydrous dichloromethane (82 ml) was added to the mixture at a temperature of from −5° to 5° C. by allowing its temperature to gradually rise to room temperature. Excess phosgene and the solvent used were evaporated to dryness under reduced pressure to give crude N-(3,4-diacetoxybenzoyl)-N-methylcarbamoyl chloride. The product was dissolved in cold anhydrous dichloromethane (50 ml) and, after removing insoluble substances by filtration, made available for the subsequent reaction.

(2) N,O-Bis(trimethylsilyl)acetamide (44.3 ml) was added to a suspension of D(−)-p-hydroxyphenylglycine (15.40 g) in anhydrous dichloromethane (150 ml) at room temperature and to the mixture was added dropwise the solution of N-(3,4-diacetoxybenzoyl)-N-methylcarbamoyl chloride in anhydrous dichloromethane previously obtained in (1) with stirring. After stirring at 5° to 10° C. for 1.5 hours, the mixture was evaporated to dryness at room temperature under reduced pressure and, after adding anhydrous methanol to the residue, the mixture was evaporated again to dryness at room temperature under reduced pressure.

Ethyl acetate (500 ml) and cold N hydrochloric acid were added to the residue, and the organic layer was separated. The layer was washed with a cold, saturated sodium chloride aqueous solution (500 ml) and extracted three times with a cold, saturated sodium bicarbonate aqueous solution in a total amount of 700 ml. The aqueous layer separated was washed three times with 100 ml ethyl acetate each and, after adjusting its pH to about 2.5 with cold 2 N hydrochloric acid, re-extracted with ethyl acetate. The organic layer separated was washed with a cold, saturated sodium chloride aqueous solution, dried over anhydrous sodium sulfate and evaporated to dryness under reduced pressure to give 14.5 g of D(−)-α-[3-(3,4-diacetoxybenzoyl)-3-methyl-1-ureido]-α-(4-hydroxyphenyl)acetic acid as a pale yellow powder.

| TLC: | Rf 0.51, silica gel 60 $F_{254}$ |
|---|---|
| | Carrier: (a pre-coated plate manufactured by E. Merck, Darmstadt) |
| | Developer: ethyl acetate-ethanol-acetic acid (25:5:1, by volume) |
| IR spectrum: | $\nu_{max}^{KBr}(cm^{-1})$ 3,700–2,300, 1,770, 1,740, 1,700–1,680, 1,510 |
| NMR spectrum: | (DMSO-$d_6$, 60MHz) δ(ppm) 2.28(6H,s) 3.12(3H,s), 5.23(1H,d, J = 7Hz), 6.6–7.6(7H,m), 9.50(1H,d, J = 7Hz) |

Color reaction with ferric chloride: positive (3) To a solution of D(−)-α-[3-(3,4-diacetoxybenzoyl)-3-methyl-1-ureido]-α-(4-hydroxyphenyl)acetic acid (2.0 g) in methanol (20 ml) was added dropwise 29% aqueous ammonia (3 ml) under cooling with ice-water followed by stirring the mixture for 30 minutes while maintaining its temperature between 0° and 5° C. After adding cold N hydrochloric acid (50 ml), the mixture was extracted with ethyl acetate (100 ml). The organic layer was separated, washed with water and extracted with a cold, saturated sodium bicarbonate aqueous solution (70 ml). The aqueous layer was separated and washed with ethyl acetate (100 ml).

After adjusting its pH to about 2.5 with cold 2 N hydrochloric acid, the aqueous layer was re-extracted with ethyl acetate (200 ml). The organic layer separated was washed with a cold, saturated sodium chloride aqueous solution, dried over anhydrous sodium sulfate, and evaporated to dryness under reduced pressure to give 1.3 g of D(−)-α-[3-(3,4-dihydroxybenzoyl)-3- methyl-1-ureido]-α-(4-hydroxyphenyl)acetic acid as a white powder.

(4) D(—)-α-[3-(3,4-Dihydroxybenzoyl)-3-methyl-1-ureido]-α-(4-hydroxyphenyl)acetic acid (0.70 g) fully dried over phosphorus pentachloride, was dissolved in anhydrous tetrahydrofuran (15 ml) containing 1-hydroxybenztriazole (0.30 g). To the solution was added dropwise 8 ml of a solution of N,N'-dicyclohexylcarbodiimide (0.48 g) in anhydrous tetrahydrofuran at 0° C. on an ice bath under a nitrogen atmosphere. The stirring was continued while allowing its temperature to gradually rise to room temperature for 2 hours and the resulting precipitate (N,N'-dicyclohexylurea) was removed by filtration. The filtrate containing 1-benzotriazolyl ester of D(—)-α-[3-(3,4-dihydroxybenzoyl)-3-methyl-1-ureido]-α-(4-hydroxyphenyl)acetic acid was made available for the subsequent reaction.

(5) N,O-Bis(trimethylsilyl)acetamide (2.0 ml) was added under a nitrogen atmosphere at 15° C. to 20° C. to a suspension of 6-aminopenicillanic acid (0.84 g) in anhydrous dichloromethane (50 ml) followed by stirring the mixture until it became clear. To the clear solution was added dropwise the solution in tetrahydrofuran previously obtained in (4) while maintaining the temperature of the mixture between 5° and 10° C., followed by stirring for 2 hours. Then, the mixture was evaporated to dryness at room temperature under reduced pressure and, after adding anhydrous methanol to the residue, evaporated again to dryness under reduced pressure. Ethyl acetate (100 ml) and cold N hydrochloric acid (80 ml) were added to the residue and the organic layer was separated. The layer was washed with a cold, saturated sodium chloride aqueous solution and extracted three times with a cold, saturated sodium bicarbonate in a total amount of 200 ml. The aqueous layer separated was washed with ethyl acetate (150 ml) and, after adjusting its pH to about 2.5 with cold 2 N hydrochloric acid, re-extracted with ethyl acetate (150 ml). The organic layer was washed with a cold, saturated sodium chloride aqueous solution, dried over anhydrous sodium sulfate and evaporated under reduced pressure. The treatment of the residue with 80 ml of n-hexane gave 0.7 g of 6-[D(—)-α-{3-(3,4-dihydroxybenzoyl)-3-methyl-1-ureido}-α-(4-hydroxyphenyl)acetamido]penicillanic acid as a pale yellow amorphous solid.

| TLC: | Rf 0.38, silica gel 60 F$_{254}$ |
|---|---|
| | Carrier: (a pre-coated plate manufactured by E. Merck, Darmstadt) |
| | Developer: ethyl acetate-ethanol-acetic acid (25:5:1, by volume) |
| | IR spectrum: $\nu_{max}^{KBr}$(cm$^{-1}$) 3,700–2,300, 1,770, 1,750–1,620 |
| | NMR spectrum: (DMSO-d$_6$, 60MHz) δ(ppm) 1.42(3H,s), 1.55(3H,s), 3.10(3H,s), 4.20(1H,s), 5.3–5.7(3H,m), 6.5–7.4(7H,m). |
| | UV spectrum: (C$_2$H$_5$OH) λmax (nm) 275, 280 (shoulder), 290 (shoulder) |
| | Color reaction with ferric chloride: positive (dark green) |

EXAMPLE 9

(1) The procedure used in Example 8 (2) was repeated except that D(—)-phenylglycine (14.00 g) was used instead of D(—)-p-hydroxyphenylglycine (15.40 g) to give 15.0 g of D(—)-α-[3-(3,4-diacetoxybenzoyl)-3-methyl-1-ureido]-α-phenylacetic acid as a pale yellow powder.

| TLC: | Rf 0.52, silica gel 60 F$_{254}$ |
|---|---|
| | Carrier: (a pre-coated plate manufactured by E. Merck, Darmstadt) |
| | Developer: ethyl acetate-ethanol-acetic acid (25:5:1, by volume) |
| | IR spectrum: $\nu_{max}^{KBr}$(cm$^{-1}$) 3,700–2,400, 1,775, 1,740, 1,700, 1,510 |
| | NMR spectrum: (DMSO-d$_6$, 60MHz) δ(ppm) 2.29(6H,s), 3.12(3H,s), 5.35(1H,d, J = 7Hz), 7.2–7.6(8H,m), 9.65(1H,d, J = Hz). |

The above compound was also prepared by the following method. To a mixture of tetrahydrofuran (50 ml), trimethylsilyl chloride (7 g) and D(—)-α-(3-methyl-1-ureido)-α-phenylacetic acid (6.4 g) prepared by reacting D(—)-phenylglycine with N-methyl isocyanate was added dropwise triethylamine (6.4 g) at a temperature below 10° C. with stirring. After completion of the addition, the mixture was stirred at 40° C. to 50° C. for 1 hour and cooled to a temperature below 10° C. To the mixture was added dropwise a solution of 3,4-diacetoxybenzoyl chloride (7.9 g) in tetrahydrofuran (20 ml) and then the mixture was stirred at 50° C. for 2 hours. After cooling to a temperature below 10° C., a small amount of methanol was added to the mixture and the insolubel substances were removed by filtration. The filtrate was evaporated to dryness at room temperature under reduced pressure and the residue was purified with a column chromatography on silica gel (Wako-gel C-200 manufactured by Wako Junyaku K.K., Japan) with 3-4% methanol in chloroform to give 5 g of the product as a white powder.

(2) The procedure used in Example 8 (3) was repeated except that D(—)-α-[3-(3,4-diacetoxybenzoyl)-3-methyl-1-ureido]-α-phenylacetic acid was used instead of D(—)-α-[3-(3,4-diacetoxybenzoyl)-3-methyl-1-ureido]-α-(4-hydroxyphenyl)acetic acid and the product was treated as described in Example 8 (4) and (5) to give 0.5 g of 6-[D(—)-α-{3-(3,4-dihydroxybenzoyl)-3-methyl-1-ureido}-α-phenylacetamido]penicillanic acid as a pale yellow amorphous solid.

| TLC: | Rf 0.39, silica gel 60 F$_{254}$ |
|---|---|
| | Carrier: (a pre-coated plate manufactured by E. Merck, Darmstadt) |
| | Developer: ethyl acetate-ethanol-acetic acid (25:5:1, by volume) |
| | IR spectrum: $\nu_{max}^{KBr}$(cm$^{-1}$) 3,700–2,300, 1,775, 1,740–1,620 |
| | NMR spectrum: (DMSO-d$_6$, 60MHz) δ(ppm) 1.41(3H,s), 1.54(3H,s), 3.10(3H,s), 4.20(1H,s), 5.3–5.8(3H,m), 6.6–7.5(8H,m). |
| | UV spectrum: (C$_2$H$_5$OH) λmax (nm) 270, 295 |
| | Color reaction with ferric chloride: positive (dark green) |

EXAMPLE 10

(1) N,O-Bis(trimethylsilyl)acetamide (11.8 ml) was added to a suspension of amoxicillin trihydrate (10.00 g) in anhydrous dichloromethane (70 ml) at 15° C. to 20°

C., followed by stirring until the mixture became clear. To the clear mixture was added dropwise 30 ml of an anhydrous dichloromethane solution of N-(3,4-diacetoxybenzoyl)-N-methylcarbamoyl chloride prepared from 4.00 g of N-methyl-3,4-diacetoxybenzamide in the manner used in Example 8 (1). After stirring for 1.5 hours at 5° C. to 10° C., the mixture was evaporated to dryness at room temperature under reduced pressure. Anhydrous methanol was added to the residue and the mixture was evaporated again to dryness under reduced pressure. Ethyl acetate (200 ml) and cold N hydrochloric acid (50 ml) were added to the residue and the organic layer was recovered. The organic layer was washed with a cold, saturated sodium chloride aqueous solution (200 ml) and extracted three times with a cold, saturated sodium bicarbonate in a total amount of 300 ml. The combined aqueous layer was washed twice with 150 ml of ethyl acetate each and, after adjusting its pH to about 2.5 with cold 2 N hydrochloric acid, re-extracted with ethyl acetate. The organic layer separated was washed with a cold, saturated sodium chloride aqueous solution, dried over anhydrous sodium sulfate, and evaporated to dryness under reduced pressure. The treatment of the residue with 50 ml of n-hexane gave 6-[D(−)-α-{3-(3,4-diacetoxybenzoyl)-3-methyl-1-ureido}-α-(4-hydroxyphenyl)acetamide]-penicillanic acid as a white powder.

| TLC: | Rf 0.40, silica gel 60 F$_{254}$ |
|---|---|
| | Carrier: (a pre-coated plate manufactured by E. Merck, Darmstadt) |
| | Developer: ethyl acetate-ethanol-acetic acid (25:5:1, by volume) |
| | IR spectrum: $\nu_{max}^{KBr}$(cm$^{-1}$) 3,700–2,300, 1,770, 1,720–1,620, 1,510 |
| | NMR spectrum: (DMSO-d$_6$, 60MHz) δ(ppm) 1.45(3H,s), 1.57(3H,s), 2.28(6H,s), 3.11(3H,s), 4.23(1H,s), 5.3–5.8(3H,m), 6.6–7.8(7H,m). |

EXAMPLE 11

The white powder (1.0 g) obtained in Example 10 was dissolved in ethanol (30 ml) and to the solution was added dropwise 29% aqueous ammonia (0.47 ml) under cooling with ice-water. After stirring at 0° C. to 5° C. for 30 minutes, the solution was poured into cold N hydrochloric acid (50 ml) and extracted with ethyl acetate (100 ml). The organic layer separated was washed with water and extracted with a cold, saturated sodium bicarbonate aqueous solution (50 ml). The aqueous layer separated was washed with ethyl acetate (50 ml) and, after adjusting its pH to about 2.5 with cold 2 N hydrochloric acid, re-extracted with ethyl acetate (100 ml). The organic layer separated was washed with a cold, saturated sodium chloride aqueous solution, dried over anhydrous sodium sulfate and evaporated to dryness under reduced pressure. The treatment of the residue with n-hexane (50 ml) gave 6-[D(−)-α-{3-(3,4-dihydroxybenzoyl)-3-methyl-1-ureido}-α-(4-hydroxyphenyl)acetamide]penicillanic acid. The IR, NMR and UV spectra, Rf value (TLC) and the result of color reaction with ferric chloride of the product were the same as those of the object product obtained in Example 8 (5).

EXAMPLE 12

The procedure used in Example 10 was repeated except that ampicillin trihydrate (9.64 g) was used instead of amoxicillin trihydrate (10.00 g) to give 6-[D(−)-α-{3-(3,4-diacetoxybenzoyl)-3-methyl-1-ureido}-α-phenylacetamido]-penicillanic acid as a white powder.

| TLC: | Rf 0.44, silica gel 60 F$_{254}$ |
|---|---|
| | Carrier: (a pre-coated plate manufactured by E. Merck, Darmstadt) |
| | Developer: ethyl acetate-ethanol-acetic acid (25:5:1, by volume) |
| | IR spectrum: $\nu_{max}^{KBr}$(cm$^{-1}$) 3,700–2,300, 1,780, 1,720–1,620, 1,510 |
| | NMR spectrum: (CDCl$_3$, 60MHz) δ(ppm) 1.48(6H,s), 2.27(6H,s), 3.18(3H,s), 4.34(1H,s), 5.35–5.75(3H,m), 7.1–7.6(8H,m). |

EXAMPLE 13

To a methanol solution (5 ml) of 6-[D(−)-α-{3-(3,4-diacetoxybenzoyl)-3-methyl-1-ureido}-α-phenylacetamido]-penicillanic acid (1.0 g) obtained in Example 12 was added dropwise 3 ml of methanolic ammonia (0.075 g/ml) while stirring and maintaining its temperature between −15° C. and −10° C. followed by continuing the stirring at the same temperature for 20 minutes. Then the reaction mixture was poured into a mixture of 5% hydrochloric acid (20 ml) and ethyl acetate (20 ml) under cooling with ice-water while stirring. The organic layer was separated and the remaining aqueous layer was extracted again with 20 ml of ethyl acetate and the organic layer separated was combined with the previously separated organic layer. The combined layer was washed with water and extracted with a cold, saturated aqueous solution of sodium bicarbonate (100 ml). The aqueous layer separated was washed with ethyl acetate and, after adjusting its pH to about 2.5 with cold 2 N hydrochloric acid, re-extracted with ethyl acetate (30 ml). The organic layer separated was washed with water, dried over anhydrous magnesium sulfate and evaporated to dryness under reduced pressure. The treatment with n-hexane (50 ml) gave 6-[D(−)-α-{3-(3,4-dihydroxybenzoyl)-3-methyl-1-ureido}-α-phenylacetamido]-penicillanic acid. The IR, NMR and UV spectra, Rf value (TLC) and the result of Color reaction with ferric chloride of the product were the same as those of the product obtained in Example 9 (2).

EXAMPLE 14

The procedure used in Example 8 (1) was repeated except that N-ethyl-3,4-diacetoxybenzamide (15.84 g) was used instead of N-methyl-3,4-diacetoxybenzamide (15.0 g) to give N-(3,4-diacetoxybenzoyl)-N-ethylcarbamoyl chloride. The product was reacted with D(−)-phenylglycine (14.00 g) and treated as in Example 8 (2) to give 14.00 g of D(−)-α-[3-(3,4-diacetoxybenzoyl)-3-ethyl-1-ureido]-α-phenyl acetic acid.

| TLC: | Rf 0.54, silica gel 60 F$_{254}$ |
|---|---|
| | Carrier: (a pre-coated plate manufactured by E. Merck, Darmstadt) |
| | Developer: ethyl acetate-ethanol- |

-continued

| | acetic acid (25:5:1, by volume) |
|---|---|
| IR spectrum: | $\nu_{max}^{KBr}(cm^{-1})$ 3,700–2,300, 1,775, 1,750, 1,700, 1,510 |
| NMR spectrum: | (CDCl$_3$, 60MHz) δ(ppm) 1.10(3H,t, J = 7Hz), 2.28(6H,s), 3.75(2H,q, J = 7Hz), 5.53(1H,d, J = 6.5Hz), 7.2–7.5(8H,m), 9.70(1H,d,J = 6.5Hz). |

(2) By the procedure used in Example 8 (3)–(5), D(—)-α-[3-(3,4-diacetoxybenzoyl)-3-ethyl-1-ureido]-α-phenylacetic acid (10.0 g) was treated to give 6-[D(—)-α-{3-(3,4-dihydroxybenzoyl)-3-ethyl-1-ureido}-α-phenylacetamido]-penicillanic acid as a white amorphous solid.

| TLC: | Rf 0.42, Carrier: | silica gel 60 F$_{254}$ (a pre-coated plate manufactured by E. Merck, Darmstadt) |
|---|---|---|
| | Developer: | ethyl acetate-ethanol-acetic acid (25:5:1, by volume) |
| | IR spectrum: | $\nu_{max}^{KBr}(cm^{-1})$ 3,700–2,300, 1,775, 1,750–1,620, 1,515 |
| | NMR spectrum: | (DMSO-d$_6$, 60MHz) δ(ppm) 0.8–1.3 (3H,m), 1.43(3H,s), 1.57(3H,s), 3.4–4.0(2H,m), 4.23(1H,s), 5.3–5.8(3H,m), 6.7–7.5(8H,m). |
| | UV spectrum: | (C$_2$H$_5$OH) λmax (mm) 265 (shoulder), 292 |
| | Color reaction with ferric chloride: | positive (dark green) |

EXAMPLE 15

(1) N-Methyl-3,4,5-triacetoxybenzamide (4.5 g) was used instead of N-methyl-3,4-diacetoxybenzamide (15.00 g) and treated by the procedure used in Example 8 (1) to give N-(3,4,5-triacetoxybenzoyl)-N-methylcarbamoyl chloride. The product was reacted with D(—)-phenylglycine (4.5 g) and treated as in Example 8 (2) to give 3.0 g of D(—)-α[3-(3,4,5-triacetoxybenzoyl)-3-methyl-1-ureido]-α-phenylacetic acid as light red powder.

| TLC: | Rf 0.51, silica gel 60 F$_{254}$ |
|---|---|
| | Carrier: (a pre-coated plate manufactured by E. Merck, Darmstadt) |
| | Developer: ethyl acetate-ethanol-acetic acid (25:5:1, by volume) |
| | IR spectrum: $\nu_{max}^{KBr}(cm^{-1})$ 3,700–2,300, 1,780, 1,750–1,570, 1,510 |
| | NMR spectrum: (CDCl$_3$, 60MHz) δ(ppm) 2.21(9H,s), 3.14(3H,s), 5.49(1H,d,J = 6.5Hz), 7.1–7.5(7H,m), 9.88(1H,d,J = 6.5Hz). |

(2) By the procedure used in Example 8 (3)–(5), D(—)-α-[3-(3,4,5-triacetoxybenzoyl)-3-methyl-1-ureido]-α-phenylacetic acid (1.1 g) was treated to give 0.4 g of 6-[D(—)-α-{3-(3,4,5-trihydroxybenzoyl)-3-methyl-1-ureido}-α-phenylacetamido]penicillanic acid as a pale brown amorphous solid.

| TLC: | Rf 0.36, silica gel 60 F$_{254}$ |
|---|---|
| | Carrier: (a pre-coated plate manufactured by E. Merck, Darmstadt) |
| | Developer: ethyl acetate-ethanol-acetic acid (25:5:1, by volume) |
| | IR spectrum: $\nu_{max}^{KBr}(cm^{-1})$ 3,700–2,200, 1,770, 1,740–1,620, 1,515 |
| | NMR spectrum: (DMSO-d$_6$, 60MHz) δ(ppm) 1.42(3H,s), 1.56(3H,s), 3.10(3H,s), 4.20(1H,s), 5.2–5.8(3H,m), 6.5(2H,s), 7.1–7.5(5H,s). |
| | UV spectrum: (C$_2$H$_5$OH) λmax (mm) 260 (shoulder), 270 (shoulder), 285 |
| | Color reaction with ferric chloride: | positive (dark blue) |

EXAMPLE 16

6-[D(—)-α-(3-Methyl-1-ureido)-α-phenylacetamido]-penicillanic acid (4 g) prepared by reacting ampicillin trihydrate (1 mole) with N-methylisocyanate (1.2 mole) was suspended in dichloromethane (40 ml) and then N,O-bis(trimethylsilyl)acetamide (5 ml) was added dropwise to the mixture under ice-cooling. After stirring the mixture to make it clear, the mixture was cooled to a temperature below 5° C. and 15 ml of a solution of 3,4-diacetoxybenzoyl chloride (3.8 g) in dichloromethane was added followed by stirring at room temperature for 5 hours. The reaction mixture was evaporated to dryness under reduced pressure and the residue was treated as described in Example 10 to give 3.5 g of 6-[D(—)-α-{3-(3,4-diacetoxybenzoyl)-3-methyl-1-ureido}-α-phenylacetamido]penicillanic acid. The IR and NMR spectra of the product were the same as those of the product obtained in Example 12.

EXAMPLE 17

D(—)-α-[3-(3,4-Diacetoxybenzoyl)-3-methyl-1-ureido]-α-phenylacetic acid (2.5 g) obtained by Example 9 (1) was suspended in dichloromethane (20 ml) and to the suspension was added dropwise N-methylmorpholine (1.4 ml) and then 3 ml of a solution of ethyl chlorocarbonate (1.42 ml) in dichloromethane. The mixture was stirred for 3 hours to give a solution of the mixed acid anhydride in dichloromethane.

Separately, triethylamine (5.3 g) was added dropwise to a suspension of 6-aminopenicillanic acid (5.8 g) in dichloromethane (30 ml), followed by stirring until the mixture became clear.

After cooling to −20° C., the clear solution was mixed with the dichloromethane solution of the mixed acid anhydride previously prepared above followed by stirring for 1.5 hours. The reaction mixture was washed with 10% hydrochloric acid and then washed several times with a saturated sodium chloride aqueous solution. The organic layer separated was dried over anhydrous magnesium sulfate and evaporated to dryness under reduced pressure to give 2.5 g of 6-[D(—)-α-{3-(3,4-diacetoxybenzoyl)-3-methyl-1-ureido}-α-phenylacetamido]penicillanic acid. The Rf value (TLC), IR and NMR spectra of the product were the same as those of the product obtained in Example 12.

EXAMPLE 18

(1) D(—)-α-[3-(3,4-Diacetoxybenzoyl)-3-methyl-1-ureido]-α-phenylacetic acid (0.50 g) obtained in Example 9 (1) and 1-hydroxybenzotriazole hydrate (0.13 g)

were dissolved in anhydrous tetrahydrofuran (10 ml). To the solution was added dropwise 5 ml of a solution of N,N'-dicyclohexylcarbodiimide (0.29 g) in anhydrous tetrahydrofuran at 0° C. on an ice bath under a nitrogen atmosphere. The stirring was continued for 2 hours while allowing the temperature of the mixture to gradually rise to room temperature and the precipitate (dicyclohexylurea) deposited was removed by filtration. The filtrate containing 1-benztriazolyl ester of D(−)-α-[3-(3,4-diacetoxybenzoyl)-3-methyl-1-ureido]-α-phenylacetic acid was made available for the subsequent reaction.

(2) N,O-Bis(trimethylsilyl)acetamide (1.2 ml) was added to a suspension of 6-aminopenicillanic acid (0.50 g) in dichloromethane (20 ml) at 0° C. under a nitrogen atmosphere followed by stirring until the mixture was made clear. To the clear solution was added dropwise all of the tetrahydrofuran solution obtained in (1) above while maintaining the temperature of the mixture between 5° and 10° C. followed by stirring at the same temperature for 1.5 hours. The mixture was evaporated to dryness at room temperature under reduced pressure and, after adding methanol to the residue, evaporated again to dryness under reduced pressure. Ethyl acetate (100 ml) and cold N hydrochloric acid (50 ml) were added to the residue and the organic layer was separated. The layer was washed with a cold, saturated sodium chloride aqueous solution and extracted three times with a cold, saturated sodium bicarbonate aqueous solution in a total amount of 150 ml. The aqueous layer separated was washed with ethyl acetate and, after adjusting the pH to about 2.5 with cold 2 N hydrochloric acid, re-extracted with ethyl acetate (150 ml). The organic layer separated was washed with a cold, saturated sodium hydrochloride aqueous solution, dried over anhydrous sodium sulfate, and evaporated to dryness under reduced pressure. The treatment of the residue with n-hexane (50 ml) gave 0.5 g of 6-[D(−)-{3-(3,4-diacetoxybenzoyl)-3-methyl-1-ureido}-α-phenylacetamido]penicillanic acid as a pale yellow amorphous solid. The Rf value (TLC), and IR and NMR spectra of the solid were the same as those of the product obtained in Example 12.

EXAMPLE 19

D(−)-α-[3-(3,4-Diacetoxybenzoyl)-3-methyl-1-ureido]-α-(4-hydroxyphenyl)acetic acid obtained in Example 8 (2) was subjected to the treatment used in Example 18 to give 6-[D(−)-α-{3-(3,4-diacetoxybenzoyl)-3-methyl-1-ureido}-α-(4-hydroxyphenyl-)acetamido]penicillanic acid. The Rf value (TLC) and IR and NMR spectra of this product were the same as those of the product obtained in Example 10.

EXAMPLE 20

(1) D(−)-α-[3-(3,4-Diacetoxybenzoyl)-3-methyl-1-ureido]-α-phenylacetic acid (20.0 g) obtained in Example 9 (1) was dissolved in anhydrous dichloromethane (50 ml) and cooled to a temperature below −15° C. To the solution was added dropwise pivalyl chloride (5.8 ml) and then triethylamine (6.6 ml) at that temperature while stirring. After being stirred for one hour, to the mixture was added dropwise while stirring at a temperature below −15° C. a dichloromethane solution of 6-aminopenicillanic acid triethylamine salt which had been prepared from 12.8 g of 6-aminopenicillanic acid. After continuing the stirring for one hour, the reaction mixture was poured into 100 ml of a cold sodium chloride aqueous solution containing 15 ml of conc. hydrochloric acid. The dichloromethane layer separated was washed several times with a cold, sodium chloride aqueous solution, dried over anhydrous magnesium sulfate and evaporated to dryness under reduced pressure. The residue was triturated in n-hexane to give 26.7 g of crude 6-[D(−)-α-(3,4-diacetoxybenzoyl)-3-methyl-1-ureido]-α-phenylacetamido penicillanic acid.

(2) The crude product (26.7 g) obtained in (1) above was dissolved in dimethylformamide (52 ml) and, after adding cold triethanolamine (26 ml) and triethylamine (18 ml), the mixture was stirred at a temperature between room temperature and 35° C. for 2 hours. After completion of the reaction, the mixture was poured into a mixture of 300 ml of ice-water, 39 ml of conc. hydrochloric acid and 140 ml of ethyl acetate. The ethyl acetate layer was recovered, washed with water and extracted under cooling with a cold saturated sodium bicarbonate aqueous solution (300 ml). After washing the aqueous layer with ethyl acetate, the aqueous layer was recovered and poured into a mixture of ice-water (200 ml) and ethyl acetate (100 ml). 6 N-Hydrochloric acid was added dropwise to the mixture with stirring to adjust its pH to 3. The ethyl acetate layer separated was washed with water, dried over magnesium sulfate and evaporated to dryness under reduced pressure. The residue was treated with n-hexane to give a crude product (16 g) which was purified by subjecting it to a column chromatography using a column filled with 480 g of Sephadex LH-20 (a hydroxypropyl derivative of a cross-linked dextran gel manufactured by Pharmacia Fine Chemicals, Sweden) and dichloromethane-acetone (1:1, by volume) as a developer to give 11.2 g of 6-[D(−)-α-{3-(3,4-dihydroxybenzoyl-3-methyl-1-ureido}-α-phenylacetamido]penicillanic acid as a white powder. The Rf value (TLC), IR, NMR and UV spectra and the result of color reaction with ferric chloride of the product were the same as those of the product obtained in Example 9 (2).

We claim:
1. A compound represented by the formula

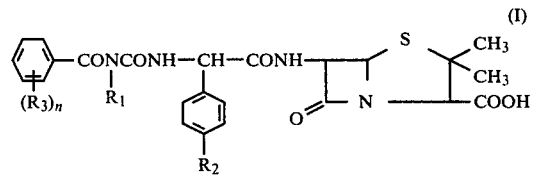

wherein $R_1$ is a hydrogen atom or a lower alkyl group; $R_2$ is a hydrogen atom or a hydroxyl group; $R_3$ is a hydroxyl group or a lower alkanoyloxyl group; n is 2 or 3; at least two of $R_3$ are bonded to adjacent carbon atoms, the position of substituent $R_3$ being selected from 3 to 5 position when $R_1$ is a lower alkyl group and $R_3$ is a hydroxyl group, and 2 to 6 position when $R_1$ and $R_3$ are other substituents, or a pharmaceutically acceptable salt thereof.

2. A compound according to claim 1 wherein $R_3$ is a hydroxyl group.

3. A compound according to claim 2 wherein $R_1$ is a hydrogen atom.

4. A compound according to claim 2 wherein $R_1$ is a lower alkyl group.

5. A compound according to claim 4 wherein the lower alkyl group is a methyl or ethyl group.

6. A compound according to claim 3 wherein $R_3$ is 2,3-dihydroxyl, 3,4-dihydroxyl or 3,4,5-trihydroxyl group.

7. A compound according to claim 4 or claim 5 wherein $R_3$ is a 3,4-dihydroxyl or 3,4,5-trihydroxyl group.

8. A compound according to claim 1 wherein $R_3$ is a lower alkanoyloxyl group.

9. A compound according to claim 8 wherein the lower alkanoyloxyl group is an acetoxyl group.

10. A compound according to claim 8 or claim 9 wherein $R_1$ is a hydrogen atom.

11. A compound according to claim 8 or claim 9 wherein $R_1$ is a lower alkyl group.

12. A compound according to claim 11 wherein the lower alkyl group is a methyl group.

13. A compound according to claim 10 wherein $R_3$ is 3,4-diacetoxyl or 3,4,5-triacetoxyl group.

14. A compound according to claim 11 wherein $R_3$ is 3,4-diacetoxyl group.

15. 6-[α-{3-(3,4,5-Trihydroxybenzoyl)-3-methyl-1-ureido}-α-phenylacetamido]penicillanic acid according to claim 1.

16. 6-[α-{3-(3,4-Dihydroxybenzoyl)-3-ethyl-1-ureido}-α-phenylacetamido]penicillanic acid according to claim 1.

17. 6-[α-{3-(3,4-Dihydroxybenzoyl)-3-methyl-1-ureido}-α-(4-hydroxyphenyl)acetamido]penicillanic acid according to claim 1.

18. 6-[α-3-(3,4-Dihydroxybenzoyl)-3-methyl-1-ureido-α-phenylacetamido]penicillanic acid according to claim 1.

19. A compound according to claim 12 wherein $R_3$ is 3,4-diacetoxyl group.

* * * * *